United States Patent [19]

Berthold et al.

[11] 4,322,437
[45] Mar. 30, 1982

[54] SPIRO SUBSTITUTED INDANONES AND TETRALONES

[75] Inventors: Richard Berthold, Bottmingen; Trevor G. Payne, Arlesheim, both of Switzerland

[73] Assignee: Sandoz Ltd., Basel, Switzerland

[21] Appl. No.: 795,439

[22] Filed: May 10, 1977

[30] Foreign Application Priority Data

May 14, 1976 [CH] Switzerland .................. 6063/76

[51] Int. Cl.³ .............. A01N 37/30; A01N 33/02; C07C 93/06
[52] U.S. Cl. ............ 424/316; 260/326.5 C; 260/348.51; 260/348.63; 260/456 P; 260/459 R; 260/501.18; 424/330; 544/230; 544/358; 544/392; 564/349; 564/351; 568/632
[58] Field of Search ............ 260/570.7, 501.18; 424/316, 330; 564/349, 351

[56] References Cited

U.S. PATENT DOCUMENTS

| | | | |
|---|---|---|---|
| 2,641,152 | 2/1972 | Shanel, Jr. et al. | 260/570.7 |
| 3,394,171 | 7/1968 | Thompson | 260/501.18 |
| 3,649,691 | 3/1972 | Shanel, Jr. et al. | 260/570.7 |
| 3,671,587 | 6/1972 | Troxler et al. | 260/570.7 |
| 3,839,415 | 10/1974 | Easton et al. | 260/570.8 X |

Primary Examiner—Robert V. Hines
Attorney, Agent, or Firm—Gerald D. Sharkin; Robert S. Honor; Thomas O. McGovern

[57] ABSTRACT

The present invention relates to a compound of formula I,

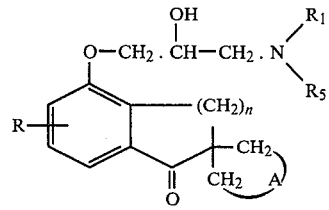

wherein
A is straight chain alkylene of 2 to 4 carbon atoms, or straight chain alkenylene of 2 to 4 carbon atoms,
n is 1, 2 or 3,
R is hydrogen or halogen of atomic number from 9 to 35, and
either (i) $R_1$ is a group of formula II,

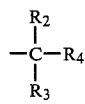

wherein
$R_2$ and $R_3$, independently, are hydrogen or alkyl of 1 to 4 carbon atoms, and
$R_4$ is alkyl of 1 to 4 carbon atoms, alkoxyalkyl of 2 to 5 carbon atoms, alkylthioalkyl of 2 to 5 carbon atoms, phenylalkyl or phenoxyalkyl or phenylthioalkyl, wherein the alkyl moiety has from 1 to 3 carbon atoms, or phenyl, the phenyl ring of each of the last four radicals being unsubstituted or mono-substituted by, or disubstituted independently by, alkyl of 1 to 4 carbon atoms, alkoxy of 1 to 4 carbon atoms, hydroxy or halogen of atomic number from 9 to 35, and
$R_5$ is hydrogen,
or (ii) $R_1$ and $R_5$ together with the nitrogen atom to which they are bound are (a) 2,2,6,6-tetramethylpiperidinyl, (b) 2,2,5,5-tetramethylpyrrolidinyl, or (c) piperazinyl substituted in the 4 position by alkyl of 1 to 4 carbon atoms or phenyl which is unsubstituted, or mono-substituted by, or di-or tri-substituted independently by, alkyl of 1 to 4 carbon atoms, alkoxy of 1 to 4 carbon atoms, or halogen of atomic number from 9 to 35, useful as anti-hypertensives.

22 Claims, No Drawings

SPIRO SUBSTITUTED INDANONES AND TETRALONES

The present invention relates to 3-amino-2-hydroxypropoxyphenyl derivatives.

The present invention provides a compound of formula I,

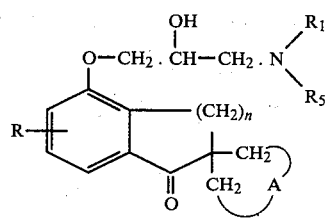

wherein
A is straight chain alkylene of 2 to 4 carbon atoms, or straight chain alkenylene of 2 to 4 carbon atoms,
n is 1, 2 or 3,
R is hydrogen or halogen of atomic number from 9 to 35, and
either (i) $R_1$ is a group of formula II,

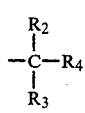

wherein
$R_2$ and $R_3$, independently, are hydrogen or alkyl of 1 to 4 carbon atoms, and
$R_4$ is alkyl of 1 to 4 carbon atoms, alkoxyalkyl of 2 to 5 carbon atoms, alkylthioalkyl of 2 to 5 carbon atoms, phenylalkyl or phenoxyalkyl or phenylthioalkyl, wherein the alkyl moiety has from 1 to 3 carbon atoms, or phenyl, the phenyl ring of each of the last four radicals being unsubstituted or mono-substituted by, or di-substituted independently by, alkyl of 1 to 4 carbon atoms, alkoxy of 1 to 4 carbon atoms, hydroxy or halogen of atomic number from 9 to 35, and
$R_5$ is hydrogen,
or (ii) $R_1$ and $R_5$ together with the nitrogen atom to which they are bound are
(a) 2,2,6,6-tetramethylpiperidinyl,
(b) 2,2,5,5-tetramethylpyrrolidinyl, or
(c) piperazinyl substituted in the 4 position by alkyl of 1 to 4 carbon atoms or phenyl which is unsubstituted, or mono-substituted by, or di- or tri-substituted independently by, alkyl of 1 to 4 carbon atoms, alkoxy of 1 to 4 carbon atoms, or halogen of atomic number from 9 to 35.

In a compound of formula I any alkyl or alkylene moiety, e.g. in alkoxyalkyl, except where otherwise stated, has preferably 2 carbon atoms or especially one carbon atom.

Halogen is preferably chlorine.

Preferably A is alkylene of 2 or 3 carbon atoms, or alkenylene of 2 carbon atoms. When A is alkenylene the double bond has the cis configuration. When A is alkenylene of 4 carbon atoms it is preferably 2-butenylene.

n is preferably 1.

R is preferably hydrogen. When it is halogen, it is preferably in the ring position meta or para to the oxygen atom attached to the phenyl ring.

$R_1$ is preferably a group of formula II. At least one of $R_2$ and $R_3$ is preferably alkyl. $R_4$ is preferably alkyl. Any phenyl ring contained in $R_1$ is preferably unsubstituted. A preferred phenyl ring substituent with regard to $R_4$ is hydroxy. $R_1$ is especially tert.-butyl.

The present invention also provides a process for the production of a compound of formula I which comprises reacting a compound of formula III,

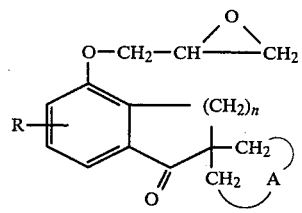

wherein A, n and R are as defined above, or a reactive functional derivative thereof, with a compound of formula IV,

wherein $R_1$ and $R_5$ are as defined above.

The reaction may be effected in conventional manner for the reaction of an epoxide or a reactive functional derivative thereof with an amine to form a β-hydroxyalkylamine.

Suitable reactive functional derivatives of the compound of formula III include compounds of formula V,

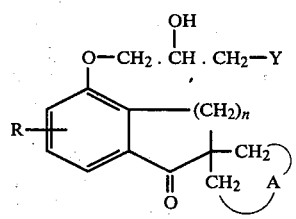

wherein
A, n, R are as defined above, and
Y is a leaving group, e.g. chlorine, bromine, iodine, mesyloxy or tosyloxy.

The reaction may be effected in an inert solvent such as dioxane. Alternatively when the amine of formula IV is liquid, this may be used as the reaction medium.

Suitable temperatures are from about 20° to about 150° C.

A compound of formula III may be obtained by reacting a compound of formula VI,

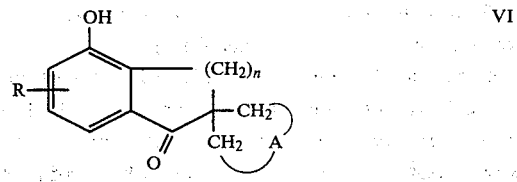

wherein A, n and R are as defined above, with epichlorohydrin in the presence of piperidine.

A compound of formula VI may obtained by demethylating or debenzylating a compound of formula VII,

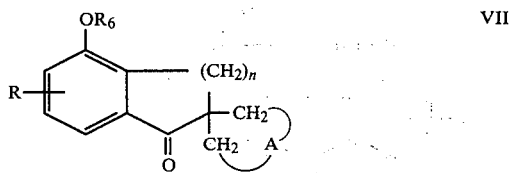

wherein
A, n and R are as defined above, and
$R_6$ is methyl or benzyl.

A compound of formula VII may be obtained by alkylating a compound of formula VIII,

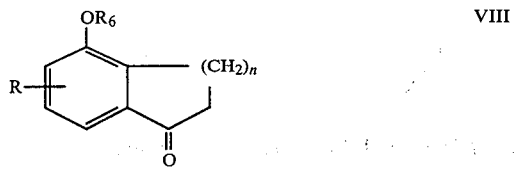

wherein
n, R and $R_6$ are as defined above, with a compound of formula IX, $$BrCH_2-A-CH_2-Br \qquad IX$$

wherein A is as defined above.

Insofar as the production of any particular starting material is not particularly described, this may be produced and purified according to known processes, or analogous to known processes. Thus a compound of formula V may be obtained by reacting a compound of formula III with a compound HY, wherein Y is as defined above.

Free base forms of the compounds of formula I may be converted into acid addition salt forms in conventional manner and vice versa. Suitable acids for salt formation include hydrochloric acid, maleic acid, malonic acid, fumaric acid and tartaric acid.

Compounds of formula I may exist in racemic or individual optical isomer form. Individual optical isomer forms may be obtained in conventional manner from the racemic form, by fractional crystallization of the tartrate diastereomeric salts. Alternatively, the individual optical isomers may be made using optically active starting materials, e.g. the compound of formula III, in a conventional stereospecific synthesis for analogous optically active 3-amino-2-hydroxy-propoxyaryl derivatives.

In the following Examples all temperatures are in degrees Centigrade and are uncorrected.

EXAMPLE 1

4'-(3-tert.-butylamino-2-hydroxypropoxy)-spiro(cyclohexane-1,2'-indan)-1'-one (1) Racemic form 7.5 g of a mixture of mainly 4'-(3-chloro-2-hydroxypropoxy)-spiro(cyclohexane-1,2'-indan)-1'-one and of 4'-(2,3-epoxypropoxy)-spiro(cyclohexane-1,2'-indan)-1'-one in 50 ml dioxane and 30 ml tert.-butylamine are heated at 130° for 20 hours in an autoclave, then cooled and partitioned between 2 N tartaric acid and ether. The aqueous phase is made alkaline and extracted with ether. The organic phases are evaporated to yield the title compound in free base form (M.Pt. 87°–88°) which is converted into the hydrogen maleate; M.Pt. 180°–181°, and hydrogen malonate M.Pt. 143°–145°.

The starting material is obtained as follows:

(a) A solution of 20 g 4-methoxyindan-1-one and 24 g 1,5-dibromopentane in 150 ml benzene is added quickly dropwise to a solution of potassium tert.-butylate (produced from 9.7 g potassium and excess tert.-butanol) in 200 ml benzene at 80°. The mixture is refluxed for 4 hours, treated with 50 ml water and 200 ml 2 N hydrochloric acid, and extracted with benzene. Chromatography on silicagel of the benzene phase gives 4'-methoxy-spiro(cyclohexane-1,2'-indan)-1'-one. M.Pt. 94°–96°.

(b) 5.6 g of 4'-methoxy-spiro(cyclohexane-1,2'-indan)-1'-one in 80 ml acetic acid and 20 ml 48% (w/w) aqueous hydrogen bromide are refluxed for 20 hours. The mixture is evaporated, diluted with water and extracted with ether. Evaporation of the solvent yields 4'-hydroxy-spiro(cyclohexane-1,2'-indan)-1'-one; M.Pt. 162°–164° (from ethanol).

(c) To 4.5 g of 4'-hydroxy-spiro(cyclohexane-1,2'-indan)-1'-one and 20 ml epichlorohydrin are added 2 drops of piperidine. The mixture is stirred at 100° for 4 hours. Evaporation and taking up of the residue in ether yields the starting material mixture as an oil on evaporation.

(2) Optically active forms 38 g of 4'-(3-tert.-butylamino-2-hydroxypropoxy)-spiro(cyclohexane-1,2-indan)-1'-one in free base form in 300 ml methanol is treated with a solution of 16.5 g L(+)-tartaric acid in 150 ml methanol. The resultant crystalline precipitate is filtered off and crystallized several times from methanol to yield 4'-[(2S)-3-tert.-butylamino-2-hydroxypropoxy]-spiro(cyclohexane-1,2'-indan)-1'-one L(+)-tartrate. M.Pt. 224°–226°. This tartrate is converted into the free base by treatment with a mixture of aqueous sodium hydroxide and ether. The free base is converted by treatment with one equivalent of malonic acid in ethanol/ether into the hydrogen malonate of the 2(S) isomer of the title compound. This compound crystallises in a solvated form (M.Pt. 64°–66°) which on drying at 60°/0.002 mm is converted to the solvent-free, higher melting product. M.Pt. 124°–126°. $[\alpha]_D^{20} = -11.4°(\pm 0.8°)$ (c=2.0 in $CHCl_3$).

The filtrate obtained on filtering off the crystalline precipitate of the L(+) tartrate salt is treated with aqueous sodium hydroxide/ether yielding a free base mixture. 32 g of this free base mixture is treated with 16.5 g D(−) tartaric acid as described in the preceding paragraph to afford 4'-[(2R)-3-tert.-butylamino-2-hydroxypropoxy)-spiro(cyclohexane-1,2'-indan)-1'-one D(−)-tartrate; M.Pt. 224°–226°, and the corresponding (2R) hydrogen malonate; M.Pt. 124°–126° $[\alpha]_D^{20} = +11.6°(\pm 0.8°)$ (c=2.0 in $CHCl_3$).

In analogous manner to Example 1, the following compounds of formula I in racemic and optically active form may be produced, wherein R=H, and

| Ex. No. | R5 | R1 | n | A | M.Pt. of racemic form |
|---|---|---|---|---|---|
| 1A | H | —C(CH3)3 | 2 | —(CH2)3— | 220°–222°[1] |
| 1B | H | —C(CH3)3 | 1 | —(CH2)2— | 220°–222°[2] |
| 1C | H | —C(CH3)3 | 2 | —(CH2)2— | 215°–217°[3] |
| 1D | H | —C(CH3)3 | 2 | —(CH2)4— | 201°–203°[2] |
| 1E | H | —C(CH3)3 | 1 | —(CH2)4— | 165°–170°[2] |
| 1F | -C(CH3)2-(CH2)2-C(CH3)2- | | 1 | —(CH2)2— | 233°–235°[3] |

[1] hydrogen maleate
[2] fumarate
[3] hydrochloride

In analogous manner to that described in Example 1 the following compounds of formula I may be produced, wherein:

| Ex. No. | R | R5 | n | A | R1 |
|---|---|---|---|---|---|
| a | 5'Cl | H | 1 | —[CH2]2— | CH2—⌬ |
| b | 6'Br | H | 1 | —[CH2]2— | —CH2—CH2—CH2—⌬(nC3H7)(nC3H7) |
| c | 7'F | H | 1 | —[CH2]2— | —CH2—CH2—O—⌬(nC3H7O)—OH |
| d | H | H | 3 | —CH=CH— | —[CH2]4S—⌬(Cl)(Br) |
| e | H | H | 3 | —CH2—CH=CH— | —[CH2]2—S—nC3H7 |
| f | H | H | 3 | —CH2—CH=CH—CH2— | —[CH2]2—O—n-C3H7 |

In analogous manner the following compounds of formula I may be produced, wherein R=H, A=—CH2—CH=CH—, n=3 and R1+R5 together with the nitrogen atom to which they are attached are:

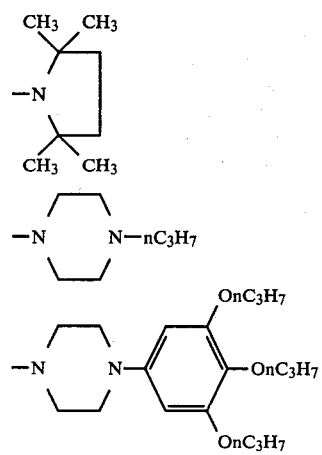

(i)

(ii)

(iii)

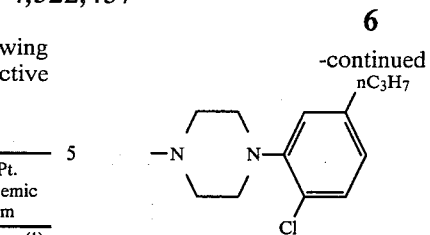

(iv)

The compounds of formula I are useful because they possess pharmacological activity in animals. In particular, the compounds are particularly useful as inhibitors of mobilisation of animal energy reserves, induced by emotional stress, e.g. by catecholamine secretion.

For example, the compounds inhibit the increased free fatty acid concentration in the blood, and the lipolysis effect, induced by emotional stress, as indicated by an inhibition of glycerol release stimulated by isoproterenol in standard tests, e.g. as follows:

(i) In vitro

Isolated fat cells are obtained from dog subcutaneous tisue, and from rat and guinea pig epididymal fat pads, in accordance with the method of M. Rodbell [J. Biol. Chem. 239, 375–380 (1964)]. Cells from one of the animals are dispersed in Krebs phosphate buffer containing 4% bovine serum albumin. 1 ml aliquots of the cell suspension in plastic incubation flasks are treated with the test substance at $10^{-9}$ to $10^{-7}$ Molar and isoproterenol at $10^{-7}$ Molar. The glycerol release is determined in conventional manner, e.g. according to the method of S. Laurell et al., Helv. Chim. Acta 13, 317–322 (1966).

(ii) In vivo

Rats are fasted for 16 hours. A sub-cutaneous injection of 400 μg/kg of isoproterenol results in a glycerol concentration in the blood plasma of 400% the original value. This increased glycerol concentration remains constant for ca. 60 minutes and acts as a control value. The test substance is administered at a dose of from about 0.001 to about 0.01 mg/kg for i.v. administration, and of from about 0.01 to about 0.1 mg/kg for p.o. administration, 10 minutes before the isoproterenol injection, and the animals are decapitated 40 minutes after the isoproterenol injection. The glycerol concentration in the blood is calculated in conventional manner, e.g. using the conventional glycero-3-phosphate-dehydrogenase method [according S. Laurell et al.; reference as mentioned above].

By virtue of their effect in reducing the increases in free fatty acid concentration in blood plasma, the compounds are therefore useful in the treatment of acute myocardial infarction in animals, resulting inter alia in a decrease in the risk of ventricular arrhythmias and further myocardial ischemic injury.

As indicated by the above, the compounds are additionally useful in the prophylaxis of myocardism in animals suffering from a myocardial ischemic injury, e.g. due to arteriosclerosis in the heart coronary arteries. Administration of the compounds prevents inter alia an increase in the ischemic zone in the heart and the anaerobic metabolic condition of the heart.

The compounds of formula I additionally inhibit hyperglycemia induced by emotional stress, as indicated by an inhibition of glycogenolysis in standard tests, as follows:

In the above-mentioned rat in vivo test the glucose concentration in the blood is determined in conventional manner, e.g. using the ferricyanide method. In the control animals the glucose concentration doubles after 40 minutes after isoproterenol administration. The compounds are administered parenterally at a dose of from about 0.01 to about 10 mg/kg animal body weight.

By virtue of their effect in the above test the compounds are therefore further useful as suppressants of appetite, e.g. induced by emotional stress. Such stress conditions are well appreciated in the art, e.g. see M. Carruthers et al., in D. M. Burley et al.: New Perspectives in beta-blockade, Int. Symposium Scanticon, Aarhus, Denmark, p. 275, 1972, and may include emotional stresses associated with car driving, speaking in public, and preparing for parachuting.

For the above-mentioned uses the dosage will, of course, vary depending on the compound employed, mode of administration and treatment desired. However, in general, satisfactory results are obtained with a daily dosage of from about 0.01 to about 10 mg/kg animal body weight, conveniently given in divided doses 2 to 4 times a day or in sustained release form. For the larger mammal, the total daily dosage is in the range from about 10 to about 500 mg, and dosage forms suitable for oral or parenteral administration comprise from about 2 to about 250 mg of the compounds admixed with a solid or liquid pharmaceutical carrier or diluent.

In addition, the compounds are useful as cardiovascular β-adrenoceptor blocking agents, e.g. for the prophylaxis and therapy of coronary diseases, particularly in the treatment of Angina pectoris, in the hyperkinetic heart syndrome and conditions resulting from muscular hypertrophic subvalvular aortic stenosis, and as anti-arrhythmic agents, e.g. for the treatment of heart rhythm disorders, as indicated in standard tests, e.g. by an inhibition of the positive inotropic adrenaline effect in the spontaneously beating guinea pig atrium at bath concentrations of from 0.005 to 3 mg/liter in accordance with the method of K. Sammeli, Helv. Physiol. Acta 25 Cr 215-221 (1967); and in the infusion test in narcotized cat at doses of approximately 0.02 to 1 mg/kg i.v., where they induce a strong, long lasting inhibition of the tachycardia and blood pressure lowering caused by isoproterenol.

In general, the 2(S) optical isomers are more active than the 2(R) optical isomers.

For the above-mentioned use, the dosage administered will, of course, vary depending on the compound employed, mode of administration and treatment desired. However, in general, satisfactory results are obtained with a daily dosage of from about 0.002 to about 3 mg/kg animal body weight, conveniently given in divided doses 2 to 4 times a day or in sustained release form. For the larger mammal, the total daily dosage is in the range of from about 2 to 500 mg, suitably from about 2 to about 100 mg, and dosage forms suitable for oral administration comprise from about 0.5 to about 250 mg, suitably from about 0.5 to about 50 mg, of the compound, admixed with a solid or liquid pharmaceutical carrier or diluent.

The compounds of formula I also exhibit a salidiuretic effect as indicated in standard tests e.g. in the diuretic rat test in accordance with the principles of E. Flückiger et al., Schweiz. med. Wschr. 1963, 93, 1232, on administration p.o. of from about 0.1 to about 50 mg/kg animal body weight of the compounds.

The compounds are therefore useful as salidiuretic agents, e.g. for the treatment of odema and hypertension.

For this use the dosage will, of course, vary depending on the compound employed, mode of administration and treatment desired. However, in general, satisfactory results are obtained when administered at a daily dosage of from about 0.1 mg to about 50 mg per kg animal body weight, conveniently given in divided doses 2 to 4 times a day or in sustained release form. For the larger mammal, the total daily dosage is in the range from about 1 to about 500 mg, and dosage forms suitable for oral administration comprise from about 0.2 mg to about 250 mg of the compounds admixed with a solid or liquid pharmaceutical carrier or diluent.

Additionally, the compounds of formula I exhibit blood-pressure lowering activity as indicated in standard tests, e.g. in the Grollman rat test on administration p.o. and s.c. of from 1 to 10 mg/kg animal body weight of the compounds.

As a result of their activity in the above test and their activity as salidiuretic agents, the compounds are therefore furthermore useful as blood-pressure lowering agents, e.g. for the treatment of high arterial blood pressure.

For this use the dosage will, of course, vary depending on the compound employed, mode of administration and treatment desired. However, in general, satisfactory results are obtained when administered at a daily dosage of from about 0.01 mg to about 10 mg per kg animal body weight, conveniently given in divided doses 2 to 4 times a day or in sustained release form. For the larger mammals, the total daily dosage is in the range from about 1 to about 100 mg, and dosage forms suitable for oral administration comprise from about 0.2 mg to about 50 mg of the compounds admixed with a solid or liquid pharmaceutical carrier or diluent.

An indicated daily dose is from about 1 to about 100 mg, conveniently administered in divided doses 2 to 4 times a day in unit dosage form containing from about 0.25 to about 50 mg of the compounds, or in sustained release form.

The compounds of Examples 1 and 1A to 1F have been found to be useful in the treatment of stress conditions and hypertension in animals on administration of from 0.1 to 10 mg/kg animal body weight per day.

The Example 1 compound exhibits particularly interesting properties.

The compounds may be administered in pharmaceutically acceptable acid addition salt form. Such forms exhibit the same order of activity as the free base forms. The present invention also provides a pharmaceutical composition comprising a compound of formula I in free base form or in pharmaceutically acceptable acid addition salt form, in association with a pharmaceutical carrier or diluent. Such compositions may be formulated in conventional manner so as to be, for example, a solution or tablet.

In a group of compounds A is conveniently alkylene and conveniently in formula II $R_2$ is other than alkoxyalkyl or alkylthioalkyl.

Compounds of formula I may comprise the following individual groups:
(i) Compounds wherein A is alkylene.
(ii) Compounds wherein A is alkenylene.
(iii) Compounds wherein n is 1.
(iv) Compounds wherein n is 2.
(v) Compounds wherein n is 3.
(vi) Compounds wherein R is hydrogen.
(vii) Compounds wherein R is halogen.
(viii) Compounds wherein $R_1$ is a radical of formula II, preferably $R_4$ being alkyl.
(ix) Compounds wherein $R_1$ and $R_5$ together with the nitrogen atom to which they are bound are a radical (ii) as defined above, with respect to formula I.

Further groups may be set up by combining a group of the significance A with at least one group of the significances chosen from n, $R_1$ and $R_1$ and $R_5$.

We claim:
1. A racemic or optically active compound of formula I,

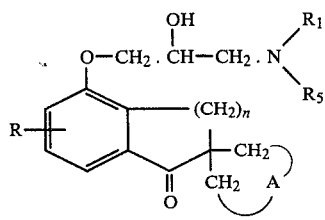

wherein
A is straight chain alkylene of 2 to 5 carbon atoms, or straight chain alkenylene of 2 to 4 carbon atoms,
n is 1, 2 or 3,
R is hydrogen or halogen of atomic number from 9 to 35, and
$R_1$ is a group of formula II,

wherein
$R_2$ and $R_3$, independently, are hydrogen or alkyl of 1 to 4 carbon atoms, and
$R_4$ is alkyl of 1 to 4 carbon atoms, alkoxyalkyl of 2 to 5 carbon atoms, alkylthioalkyl of 2 to 5 carbon atoms, phenylalkyl or phenoxyalkyl or phenylthioalkyl, wherein the alkyl moiety has from 1 to 3 carbon atoms, or phenyl, the phenyl ring of each of the last four radicals being unsubstituted or mono-substituted by, or disubstituted independently by, alkyl of 1 to 4 carbon atoms, alkoxy of 1 to 4 carbon atoms, hydroxy or halogen of atomic number from 9 to 35, and
$R_5$ is hydrogen,
or a pharmaceutically acceptable acid addition salt thereof.

2. A compound of claim 1, wherein R is hydrogen.
3. A compound of claim 2, wherein A is straight chain alkylene.
4. A compound of claim 1, wherein R is hydrogen, A is straight chain alkylene and $R_1$ and $R_5$ are as defined in claim 1 with the proviso that in formula II $R_4$ is other than alkoxyalkyl or alkylthioalkyl.
5. A compound of claim 1, which is 4'-(3-tert.-butylamino-2-hydroxypropoxy)-spiro(cyclohexane-1,2-indan)-1'-one.
6. A compound of claim 2, wherein $R_5$ is hydrogen.
7. A pharmaceutical composition comprising a therapeutically effective amount of a compound of claim 1, in association with a pharmaceutical carrier or diluent.
8. A method of treating a coronary disease selected from myocardial infarction, hyperlipidemia or hyperglycemia or appetite induced by emotional stress, angina pectoris, hyperkinetic heart syndromes, muscular hypertrophic subvalvular aortic stenosis, heart rhythm disorders, hypertension, and high arterial blood pressure, in an animal, comprising administering a therapeutically effective amount of a compound of claim 1 to said animal in need of such treatment.
9. A pharmaceutical composition according to claim 7 in which the compound is 4'-(3-tert.-butylamino-2-hydroxypropoxy)-spiro(cyclohexane-1,2-indan)-1'-one.
10. A compound of claim 6, wherein $R_1$ is —$C(CH_3)_3$—.
11. A compound of claim 10, wherein n and A are respectively 2 and —$(CH_2)_3$—.
12. A compound of claim 10, wherein n and A are respectively 1 and —$(CH_2)_2$—.
13. A compound of claim 10, wherein n and A are respectively 2 and —$(CH_2)_2$—.
14. A compound of claim 10, wherein n and A are respectively 2 and —$(CH_2)_4$—.
15. A compound of claim 10, wherein n and A are respectively 1 and —$(CH_2)_4$—.
16. A compound of claim 1 in racemic form.
17. A compound of claim 1 in 2(S) form.
18. A compound of claim 1 in 2(R) form.
19. A compound of claim 17 which is 2(S) 4'-(3-tert.-butylamino-2-hydroxypropoxy)-spiro(cyclohexane-1,2'-indan)-1'-one.
20. A compound of claim 18 which is 2(R) 4'-(3-tert.-butylamino-2-hydroxypropoxy)-spiro(cyclohexane-1,2'-indan)-1'-one.
21. A compound according to claim 1 in free base form.
22. A compound according to claim 1 in acid addition salt form.

* * * * *